(12) United States Patent
Howard et al.

(10) Patent No.: US 8,669,383 B2
(45) Date of Patent: *Mar. 11, 2014

(54) PREPARATION OF AMINOMETHYL FURANS AND ALKOXYMETHYL FURAN DERIVATIVES FROM CARBOHYDRATES

(75) Inventors: Stephen Howard, Sherman, IL (US); Alexandra Sanborn, Lincoln, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/994,170

(22) PCT Filed: Dec. 13, 2011

(86) PCT No.: PCT/US2011/064513
§ 371 (c)(1),
(2), (4) Date: Jun. 14, 2013

(87) PCT Pub. No.: WO2012/082665
PCT Pub. Date: Jun. 21, 2012

(65) Prior Publication Data
US 2013/0303791 A1    Nov. 14, 2013

Related U.S. Application Data

(60) Provisional application No. 61/423,684, filed on Dec. 16, 2010.

(51) Int. Cl.
*C07D 307/04* (2006.01)
*C07D 307/34* (2006.01)

(52) U.S. Cl.
USPC ............................... 549/491; 549/429

(58) Field of Classification Search
USPC .................................... 549/429, 491
See application file for complete search history.

(56) References Cited

U.S. PATENT DOCUMENTS 5,344,974 A * 9/1994 Descotes et al. .............. 562/567
7,572,925 B2 * 8/2009 Dumesic et al. .............. 549/488

* cited by examiner

*Primary Examiner* — Golam M M Shameem
(74) *Attorney, Agent, or Firm* — Mark W. Roberts; Alexandra Sanborn

(57) ABSTRACT

Described herein are single step methods of making various classes of alkylamine derivatives of furan and tetrahydrofuran by simultaneous contact of a sugar with $H_2$, an acid catalyst and hydrogenation catalyst in the presence of an alkylamide solvent. The hydrogenation catalyst is a heterogeneous catalyst comprising a metal selected from the group consisting of Pt, Pd, and nickel. The acid catalysts may be homogeneous mineral acid or a heterogeneous acid catalyst on substrate. In a preferred practice the two catalysts are provided on a common heterogeneous bifunctional support. Using similar combinations of acid and hydrogenation catalysts, there is also described single step methods for making furandimethanol by simultaneously contacting a hexose with the two separate catalysts in the presence of $H_2$ in an aprotic solvent, such as dimethylformamide. With the same catalyst system and similar reaction conditions, 2, 5 furan dialkylethers can also be made in a single step when the solvent includes an ROH alcohol.

23 Claims, 1 Drawing Sheet

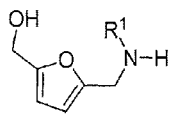

5-[(mono-alkylamino)methyl]furfuryl alcohol

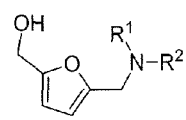

5-[(di-alkylamino)methyl] furfuryl alcohol

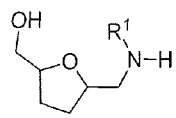

5-[(mono-alkylamino)methyl] 2-tetrahydrofurfuryl alcohol

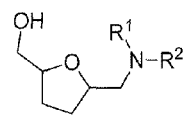

5-[(di-alkylamino)methyl] 2-tetrahydrofurfuryl alcohol

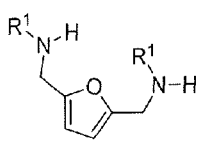

2,5-bis(mono-alkylaminomethyl)furan

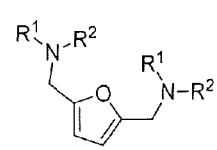

2,5-bis(dialkylaminomethyl)furan

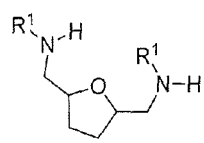

2,5-bis(mono-alkylaminomethyl)tetrahydrofuran

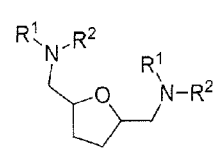

2,5-bis(dialkylaminomethyl)tetrahydrofuran

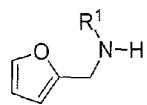

5-[(mono-alkylamino)methyl]furan

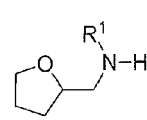

5-[(di-alkylamino)methyl] furan

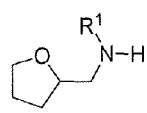

5-[(mono-alkylamino)methyl] 2-tetrahydrofuran

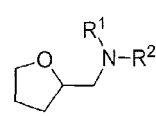

5-[(di-alkylamino)methyl] 2-tetrahydrofuran

PREPARATION OF AMINOMETHYL FURANS AND ALKOXYMETHYL FURAN DERIVATIVES FROM CARBOHYDRATES

CROSS REFERENCE TO RELATED APPLICATIONS

This application claims priority to U.S. provisional application No: 61/423,684 filed Dec. 16, 2010.

BACKGROUND OF THE INVENTION

The compound 5-(hydroxymethyl)furfural (HMF) is an important intermediate substance readily made from renewable resources, specifically carbohydrates.

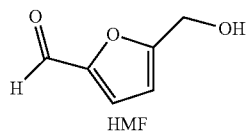

HMF

HMF is a suitable starting material for the formation of various furan ring derivatives that are known intermediates for a variety chemical syntheses, and as potential substitutes for benzene based compounds ordinarily derived from petroleum resources. Due to its various functionalities, it has been proposed that HMF could be utilized to produce a wide range of products such as polymers, solvents, surfactants, pharmaceuticals, and plant protection agents. As substitutes, one may compare derivatives of HMF to chemicals with the corresponding benzene-based rings or to other compounds containing a furan or tetrahydrofuran. HMF and 2,5-disubstituted furans and tetrahydrofuran derivatives, therefore, have great potential in the field of intermediate chemicals from renewable agricultural resources. In order to compete with petroleum based derivatives, however, preparation of HMF derivatives from common agricultural source materials, such as sugars, must be economical.

One of the concerns with HMF, is that it has limited uses as a chemical per se, other than as a source for making derivatives. Furthermore, HMF itself is rather unstable and tends to polymerize and or oxidize with prolonged storage. Due to the instability and limited applications of HMF itself, studies have broadened to include the synthesis and purification of a variety of HMF derivatives. Two derivatives of particular interest include the reduced HMF forms furan-2,5-dimethanol (FDM) and 2,5-bis-(hydroxymethyl)tetrahydrofuran (THF-diol).

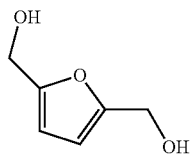

Furan-2,5-dimethanol (FDM)    2,5-bis-(hydroxymethyl)tetrahydrofuran (THF-diol)

These derivatives have been successfully synthesized in two steps involving the dehydration of fructose to HMF, followed by purification, and subsequent hydrogenation of the purified HMF (see US. Pat. No. 7,317,116). Studies have shown HMF, however, that as mentioned above, HMF itself is unstable and is also somewhat difficult to isolate. It would be useful to find a route to synthesis FDM, THF-diol and ether derivatives that did not require the intermediate step of purifying HMF.

Other derivatives of interest include HMF secondary and tertiary amines. This class of compounds is useful, for example, as a building block for pharmaceuticals such as ranitidine or Zantac™, which is a well known antiulcer drug. The traditional synthetic route for making ranitidine is according to the following series of reactions:

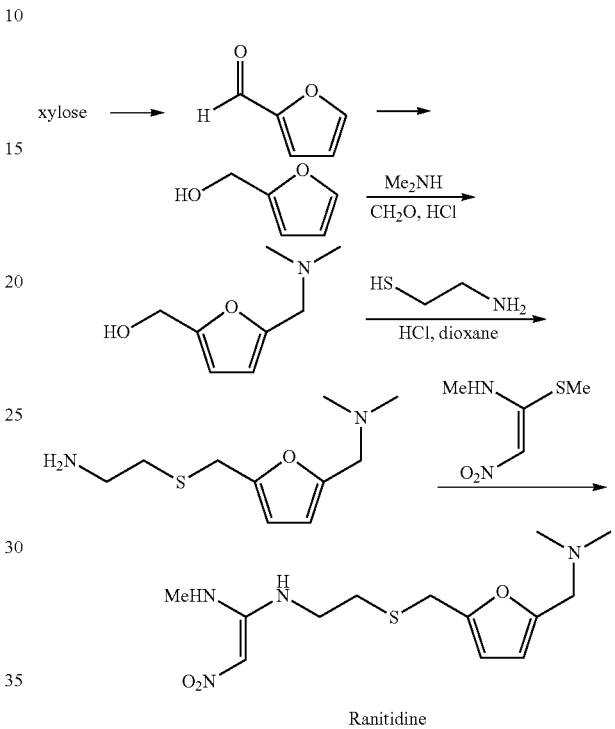

Ranitidine

The fourth compound in this reaction sequence is the HMF derivative 5'-[(dimethylamino)methyl]furfuryl alcohol, which is ordinarily made by reacting 2-hydroxymethyl furan with dimethylamine and formaldehyde as shown in the first line above. The method requires 3 steps to obtain the HMF amine derivative and the use of two hazardous chemicals, dimethylamine and formaldehyde. Dimethylamine is ranked as one of the most the most hazardous compounds (worst 10%) to ecosystems and human health. Formaldehyde also poses health risks with a recommended airborne exposure limit of 0.75 ppm averaged over an 8-hour work shift by the National Institute for Occupational Safety and Health. The National Institute for Occupational Safety and Health's currently sets the short-term exposure limit at 0.1 ppm for 15 minutes. Methods which do not expose humans and the environment to these toxic chemicals are desired for large scale production.

Other furanic secondary and tertiary amines compounds that can be derived from HMF are useful for other purposes, for example, resins, surfactants, and antimicrobial agents. Accordingly, there is a need in the art for efficient and cost effective methods to make FDM, HMF ethers and furanic alkylamino derivatives from inexpensive and less hazardous starting materials.

SUMMARY OF THE INVENTION

The HMF amine derivative, 5-[(dimethylamino)methyl]-furfuryl alcohol, has been successfully synthesized from hexose in single step reaction that uses the simultaneous combination of an acid catalyst and hydrogenation catalyst in the presence of $H_2$ and a polar aprotic solvent. The aprotic solvent exemplified herein is dimethylformamide, however other aprotic solvents could also be used. The two catalysts may be a homogeneous mineral acid catalyst and heterogeneous hydrogenation catalysts, two separate heterogeneous catalysts, one providing the acid functionality and the other the hydrogenation functionality, or most advantageously, using a bifunctional catalyst containing both a metal such as Pt, Pd, and/or Ni for hydrogenation and an acid functionality for acid catalyzed dehydration. The temperature for performing this reaction is between about 90 and 120° C. and the pressure is about 200-600 psi In a similar system, diether derivatives of HMF can also be made using similar reactions where a $C_1$-$C_4$ alcohol is used as the solvent instead of the polar aprotic solvent. These reactions can be performed with the same type of simultaneous catalyst systems described above, but at a temperature of about 100-190° C. at ordinary atmospheric pressure, or in a sealed vessel without the added of $H_2$.

Conversion of the sugar to HMF is accompanied by hydrolysis of the amide solvent, producing an amine functionality which reacts with the aldehyde of HMF generating an imine. The presence of hydrogen and catalyst reduces the imine to an amine yielding the secondary or tertiary amine derivative.

These reactions can be performed with any sugar source including hexoses and pentoses, as well as disaccharides and oligosaccharides of the same.

BRIEF DESCRIPTION OF THE DRAWINGS

FIG. 1 shows subclasses and nomenclature for certain alkyl amide derivatives made according to one aspect of the present disclosure.

DETAILED DESCRIPTION

The present invention is directed most generally, to the discovery that sugars, and most particularly hexoses and pentoses, can be simultaneously dehydrated, reduced, and derivatized to make furan and/or tetrahydrofuran derivatives in a one pot reaction that includes simultaneously contacting the sugar with a hydrogenation catalyst and an acid based catalyst in the presence of hydrogen and a solvent. The selection of the sugar, the solvent and the time, temperature and pressure conditions for the reaction can result in several different classes of derivatized furan or tetrahydrofuran compounds. These can be divided into two aspects: 1) the production of aminomethyl furans or aminomethyl tetrahydrofurans, and 2) the production of furan or tetrahydrofuran dimethanol and ethers thereof.

I Aminomethyl Furan and Aminomethyl Tetrahydrofuran

In a first aspect, there is a method of making either an aminomethylfuran or an aminomethyltetrahydrofuran derivative of the general formulae:

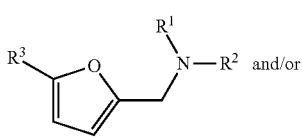

and/or

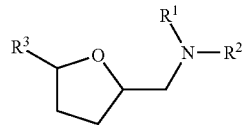

where $R^1$ is a $C_1$-$C_4$ alkyl group, $R^2$ is a $C_1$-$C_4$ alkyl group or H, and $R^3$ is H, hydroxymethyl, alkoxymethyl or acyloxymethyl. Compounds of group I may be generally called alkylaminomethyl furans, where the amine is mono- or dialkylated. Compounds of group II may generally be called alkylaminomethyl tetrahydrofurans. As will be stated in more detail hereafter, the difference between group I and group II compounds is the degree of reduction of the furan, with the group II compound being fully reduced to the tetrahydrofuran.

When the sugar is a hexose or a disaccharide, trisaccharide or oligosaccharide of hexoses, then $R^3$ is a hydroxymethyl, alkoxymethyl or acyloxymethyl group and the compounds of group I would be more specifically denoted alkylamino furans and the compounds of group II would be more specifically denoted alkylamino tetrahydrofurans. When the sugar is a pentose or a disaccharide, trisaccharide or oligosaccharide of pentoses, then $R^3$ is H.

While the foregoing nomenclature is generalized for the group I and group II compounds as a class that can be made by the processes of the present invention, specific subclasses of compounds may have other alternative names that would be synonymous with the foregoing general names. An example of some specific classes of the group I and group II compounds with alternative nomenclature that can be made by the methods described herein are shown in FIG. 1.

To obtain molecules of group I and group II, the primary solvent for the reaction system is an amide compound of the general formula:

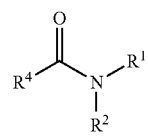

where $R^4$ is H, methyl or ethyl, and $R^1$ and $R^2$ are as previously stated. When $R^4$ is H and $R^1$ and $R^2$ are methyl, for example, the solvent is dimethylformamide (DMF), which is one preferred primary solvent that is readily available in commerce. When $R^4$ is methyl and $R^1$ and $R^2$ are methyl, the solvent is dimethyl acetamide (DMAC) which is another preferred solvent readily available in commerce. These solvents will react to reductively aminate the sugar to produce the dimethylamino species of the group I and group II molecules. When $R^4$ is H, $R^1$ is methyl, and $R^2$ is H, the solvent is formamide, which is another primary solvent readily available in commerce. When $R^2$ is H the reaction product will be the monomethylamino species of the group I and group II molecules. As indicated above the size of the $R^1$ and $R^2$ alkyl groups may be as long as $C_4$. The size limitation of these alkyl groups for the solvent is only dictated by the solubility of the sugar and the alkylamino furan or tetrahydrofuran products in the primary solvent. In principle however, $R^1$ and $R^2$ can be larger if appropriate co-solvents are used to ensure solubility of the reacting sugar and end products.

As used herein "primary solvent" means the weight of the solvent is at least equal to the weight of the reacting sugar. In various embodiments, the primary solvent represents at least 60%, more preferably at least 80% and more preferably 100% of the added solvent in the system, the last case meaning it is the only solvent added to the system not accounting for solvents that may be present with the sugar or as part of the catalyst. By way of clarity, in reactions where the acid catalyst is a homogeneous mineral acid, the mineral acid is typically an aqueous solution but the water content thereof would not be counted as a solvent per se within the present meaning of the primary solvent being the only added solvent.

Other than the primary solvent, the remaining content of the solvent system may be incidental impurities, or a co-solvent that is miscible with the primary solvent, or a carrier for the catalyst, such as in the case of a homogeneous mineral acid. Any co-solvent should be non reactive under the conditions of pressure and heat in the presence of the $H_2$ and the acid and hydrogenation catalysts used to promote the reaction. Low molecular weight (i.e., non-polymeric) alcohols, aldehydes and organic acid solvents should be avoided as the functional groups on these solvents may cause undesired side reactions. However, certain inert co-solvents such as polyethylene glycols can be used advantageously without perturbing the reaction with the amide solvent. Water may be used in small amounts, including incidental water associated with the sugar or solution of the sugar such as when the sugar is provided as an aqueous syrup solution; however the reaction itself proceeds with an acid catalyzed dehydration of the sugar which adds water to the solvent system. The generated water in turn, facilitates hydrolysis of the amide bond of the solvent, which in the presence of hydrogen and the hydrogenation catalysts reduces an imine intermediate to the amine product. Too much water however, may slow the reductive amination. Accordingly, the total of amount of water in the reaction system, including that which may be provided by the acid catalyst should, preferably, but not necessarily, be not more than 50% wt/wt.

The temperature and pressure needed to produce the group I and group II products from sugars is about 130° C. to 200° C., and at least 500 psi, respectively. In exemplary embodiments the pressure is 800 to 1000 psi. The only upper limitation on pressure is what the reactor can bear so higher pressures can be used if desired. There is a practical upper limit on temperature, because temperatures greater than about 200° C. will cause char formation. A temperature of about 180° C. is preferred. There is also a chemical reason for the lower limit on the temperature because as discussed below for another aspect of the invention, temperatures below about 130° C. can lead to the preferential formation of another class of reaction products, which can vary dependent on whether the solvent is the amide alone or an amide with an alcohol co-solvent.

It should be noted that because of the high pressure and temperatures used in the reactions and the presence of acid, any monosaccharide, disaccharide or even oligosaccharide sugars can be used as the starting material. The reaction with the acid catalyst produces water in the dehydration of the sugar. The water and acid in combination also will hydrolyze glycoside bonds especially at the temperatures and pressures used for the reductive amination. Accordingly, suitable sugars include but are not limited to monosaccharides, disaccharides, oligosaccharides and various polysaccharides. Combinations of saccharides or aqueous syrups thereof are also suitable starting materials. The syrups should preferably have a sugar solids content of at least 35% on wt/vol basis. Suitable starting materials include for example, a high fructose corn syrup product (HFCS), HFCS 42 (containing about 42 percent fructose and about 53 percent glucose), HFCS 90 (made from HFCS 42 by additional purification, about 90 percent fructose and about 5 percent each of glucose and maltose) or HFCS 55 (containing about 55 percent fructose, conventionally made from blending HFCS 42 and HFCS 90, cane syrup, beet syrup or their molasses, which contain principally sucrose. As stated herein before, the catalysts used simultaneously are a combination of an acid catalyst which promotes dehydration of the sugar, and a hydrogenation catalyst (e.g., Pt, Pd, and/or Ni), which promotes reductive amination of the dehydrated sugar.

In some embodiments the acid catalyst is a homogeneous catalyst, such as a mineral acid. Suitable mineral acid catalysts include sulfuric acid, hydrochloric acid, phosphoric acid and the like. Typically, the mineral acid catalyst is in concentrated form and added to the reaction mixture neat (i.e., at the highest available concentration which is typically 11-18 M), in which case the acid catalyst should be present at about 0.5 to 5% wt/wt basis of the sugar. Of course more dilute acids may also be used provided the acidity in the reaction mixture would be the same as adding 0.5 to 5% wt/wt of the concentrated acid. In exemplary embodiments, the mineral acid is concentrated sulfuric acid present at about 2% wt/wt of the sugar. The acid catalyst may also comprise a homogeneous acid including but not limited to p-toluenesulfonic acid and p-methanesulfonic acid.

In other embodiments the acid catalyst can be a heterogeneous acid catalyst, which is solid material having an acidic group bound therto. The solid material can be comprised of materials selected from acid clays, silicas, sulfated zirconia, molecular sieves, zeolites, ion exchange resins, heteropolyacids, carbon, tin oxide, niobia, titania and combinations thereof. Typically the substrate is a polymeric resin material such as polystyrene. The ion exchange resin may also be a sulfonated divinylbenzene/styrene copolymer resin. Some of these resin based catalysts are ordinarily used for cation exchange chromatography. Perhaps the most common acid group for cation exchange resins and other heterogeneous acid catalyst is a sulfonic group. Suitable examples of heterogeneous acid catalyst containing a sulfonic group are Amberlyst 35, Amberlyst 15, Amberlyst 36, Amberlyst 70, XN1010, IRC76, and XE586 (Rohm & Haas), RCP21H (Mitsubishi Chemical Corp.), Dowex 50WX4 (Dow Chemical Co.), AG50W-X12 (Bio-Rad), and Lewatit S2328, Lweatit K2431, Lewatit S2568, Lewatit K2629 (Bayer Corporation), HPK25 (Mitsubishi), Nafion-50 (DuPont). Other acid groups bound to substrates may also be used as the heterogeneous acid catalyst. Suitable examples of other acidic heterogeneous acid catalyst include CRP-200 phosphonic/polystyrene (Rohm & Haas).

The hydrogenation catalyst is one containing a metal that is Pt, Pd, or Ni, however, Co, Cu, Ru, Re, Rh, Ir, Fe and/or combinations of the same, with or without a promoter metal may also be employed. In some embodiments, the metal may be added to the mixture as a heterogeneous particulate powder. In more typical embodiments, the metal is bound to a substrate forming a heterogeneous metal catalyst substrate. Typical substrates include, but are not limited to kieselguhr, diatomaceous earth, silica and polymeric resin materials. One exemplary metal catalyst is represented by G-69B, available from Sud-Chemie, (Louisville, Ky.) which is a powdered catalyst having an average particle size of 10-14 microns containing nominally 62% Nickel on kieselguhr, with a Zr promoter. Other suitable catalysts containing Ni include, but are not limited to, sponge nickel and G-96B also available from Sud-Chemie Corp. G-96B is a nickel on silica/alumina, 66% nickel by weight, particle size 6-8 microns. Another preferred nickel catalyst is G-49B available from Sud-Chemie Corp. Particle size is 7-11 microns and 55% nickel by weight. Another preferred catalyst is palladium on carbon, exemplified by the catalyst Pd/C. Another preferred catalyst is G22/2 also available from Sud-Chemie Corp. G22/2 is a barium promoted copper chromite catalyst, 39% Cu and 24% Cr. In yet another embodiment the catalyst can be a platinum catalyst, exemplified by the catalyst Pt/C. In a preferred embodiment, the acid catalyst and the hydrogenation catalyst are provided on the same substrate, forming a heterogeneous bifunctional catalyst. Exemplary catalyst of this nature include Amberlyst™ CH10 and CH28, each available from Rohm and Haas Company (Midland, Mich.). Amberlyst CH10 is a macroreticular palladium metal hydrogenation resin containing sulfonic acid as the acid component. Amberlyst CH28 is a macroreticular styrene DVB copolymer palladium doped hydrogenation resin also containing sulfonic acid as the acid component. The present invention utilizes these exemplary resins as bifunctional catalysts, i.e., the palladium catalyzes hydrogenation, while the sulfonic acid promotes dehydration in one pot. This use of a bifunctional catalyst system for conversion of sugars to furan or tetrahydrofuran derivatives provides for efficient one pot conversion of sugars into useful chemicals.

The amount of hydrogenation catalyst to use can be readily optimized based on the teachings provided herein. Generally, the hydrogenation catalyst on whatever support used, should be present at about 1% to about 40% wt/wt of the amount of sugar being converted. In exemplary embodiments the Ni catalyst G-69B was used at 5% wt/wt the amount of sugar in the reaction mixture, while the bifunctional catalysts CH28 or CH10 were used at 20-33% of the weight of sugar being converted. Using any of the several embodiments of catalysts indicated above, molecules of group I or II can be made as the principle product of a sugar. The difference in conditions for obtaining the group I and group II compounds is principally time, although higher $H_2$ pressure and hydrogenation catalyst selection will also enhance further reduction. The group I aminomethyl furans are less reduced than the group II aminomethyl tetrahydrofurans. Accordingly, in a reaction sequence the group I compounds will be formed first. Under an exemplary reaction at 175-180° C., 800-1000 psi, in the presence of DMF as the solvent with fructose as the sugar using a nickel containing hydrogenation catalyst such as G-69B resin and sulfuric acid as the acid catalyst, the dominant product will be the group I aminomethyl furans after 1.5 to 3 hours of reaction time. If the reaction proceeds further, the furan derivative will become further reduced to the group II aminomethyl tetrahydrofuran derivatives. Similarly, a more active hydrogenation catalyst can produce group II compounds in shorter amount of time. It was observed that the reactions that produce the group I aminomethyl furans and group II aminomethyl tetrahydrofurans also may result in the production of smaller amounts of secondary-products, which are bis (amine) derivatives of the group I and group II compounds. Accordingly, another aspect of the present disclosure is use of the aforementioned methods to produce the following class of compounds:

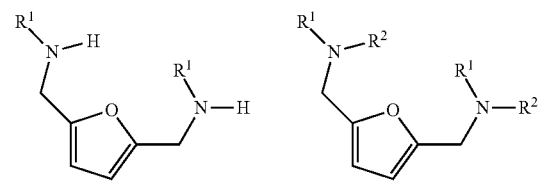

2,5-bis(mono-alkylaminomethyl)furan   2,5-bis(dialkylaminomethyl)furan

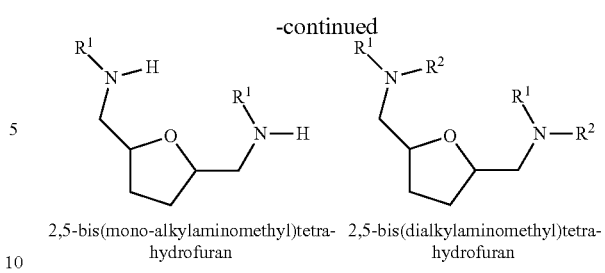

2,5-bis(mono-alkylaminomethyl)tetra-   2,5-bis(dialkylaminomethyl)tetra-
hydrofuran                             hydrofuran These bis(amine) derivatives of the group I and group II compounds are made when the sugar is a hexose, in which case $R^3$ is hydoxymethyl and the alcohol moiety $R^3$ is also subject to reductive amination. Reaction conditions that include use of stronger acids, dryer conditions (have less water) and longer times seem to improve formation of these bis(amine) derivatives.

Taking these together with the compounds shown in FIG. 1, when the sugar is a hexose or a saccharide thereof, the first aspect of the present invention is capable of making one or more classes of compounds from the following list: 5-[(mono-alkylamino)methyl]furfuryl alcohol, 5-[(di-alkylamino)methyl]furfuryl alcohol, 5-[(mono-alkylamino)methyl]2-tetrahydrofurfuryl alcohol, 5-[(di-alkylamino)methyl] 2-tetrahydrofurfuryl alcohol, bis(mono-alkylaminomethyl) furan, bis(dialkylaminomethyl)furan, bis(mono-alkylaminomethyl)tetrahydrofuran, bis (dialkylaminomethyl)furan and bis(dialkylaminomethyl) tetrahydrofuran.

When the sugar is a pentose or a saccharide thereof, the first aspect of the present invention is also capable of making one or more compounds from the following list: 5-[(mono-alkylamino)methyl]furan, 5-[(di-alkylamino)methyl]furan, 5-[(mono-alkylamino)methyl]2-tetrahydrofuran and 5-[(di-alkylamino)methyl]2-tetrahydrofuran.

II Furan and Tetrahydrofuran Dimethanol and Ethers

It also was discovered that with a hexose sugar, when DMF was used as the solvent, with bifunctional catalyst, when the temperature was less than 130° C. and the pressure was 600 psi or less, but otherwise under similar reaction conditions described above for making the alkylamine derivatives, that instead of the alkylamine, furan dimethanol and tetrahydrofuran dimethanol were made having the formulae:

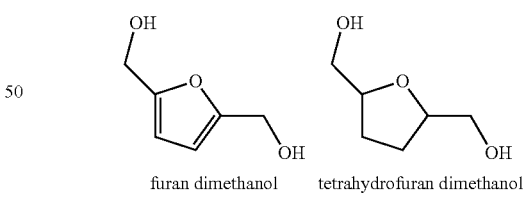

furan dimethanol    tetrahydrofuran dimethanol

These dimethanol compounds are formed when the sugar is a hexose. If the sugar is a pentose the mono methanol-furan and monomethanol tetrahydrofuan derivatives are made instead.

To make furan dimethanol, the hexose is contacted with $H_2$, a bifunctional catalyst containing a metal in the presence of DMF at temperature of between about 90 and 120° C. and a pressure of between about 200 to 600 psi for a time sufficient to produce furan dimethanol In exemplary embodiments, the temperature was 100° C., the pressure was 500 psi, and the time was three hours. To make the tetrahydrofuran dimethanol, the time and/or pressure should be longer/higher. When the solvent system lacks the amide solvent but instead contains an alcohol R'OH where R is $C_1$-$C_4$ alkyl, the product is a dialkyl ether of the furan or dialkyl ether of tetrahydrofuran according to group III or group IV, respectively.

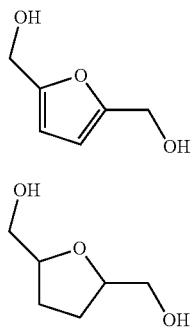

The following examples are provided as illustrations to teach one of ordinary skill in the art some basic methods for practicing the inventions of the present disclosure, with the recognition that altering parameters and conditions, for example by changing temperature, time and reagent amounts and particular amides, alcohols, sugars and specific catalysts and amounts thereof, the full practice of the invention can be extended beyond the limits of the examples provided for illustrative purposes.

EXAMPLE 1

Preparation of Aminomethylfurans from Fructose using a Combination of Catalsts This example illustrates the combination of single catalysts on the simultaneous dehydration of fructose to HMF followed by reductive amination. Crystalline fructose (10 g) was placed in a 100 mL reaction vessel with DMF (60 mL) and G-69B catalyst from Sud Chemie (0.50 g) and sulfuric acid (0.20 mL) and pressurized to 800 psi hydrogen. The solution was heated to 180° C. for 1.5 hours. The reaction was allowed to cool to ambient temperature and filtered to remove the catalyst. GC/MS analysis showed formation of 5-[(dimethylamino)methyl]-furfuryl alcohol as the major product and bis(dimethylaminomethyl)furan as a secondary by-product.

EXAMPLE 2

Preparation of Aminomethylfurans from Fructose using a Combination of Catalysts This example illustrates the combination of single catalysts on the simultaneous dehydration of fructose to HMF followed by reductive amination. Crystalline fructose (30 g) was placed in a 1000 mL reaction vessel with DMF (300 mL) and G-69B catalyst from Sud Chemie (2.40 g) and sulfuric acid (0.60 mL) and pressurized to 800 psi hydrogen. The solution was heated to 175° C. for 2 hours. The reaction was allowed to cool to ambient temperature and filtered to remove the catalyst. GC/MS showed formation of 5-[(dimethylamino)methyl]-furfuryl alcohol.

EXAMPLE 3

Synthesis of Aminomethylfurans from Fructose using Bifunctional Catalysts

Crystalline fructose (30 g) was placed in a 1 L reaction vessel with dimethylformamide (300 g) and CH10 resin (10 g). The solution was heated to 140-150° C. for 2 hours. The solution was allowed to cool to room temperature and filtered to remove the resin catalyst. GC/MS and 1H NMR supported the formation of 5-[(dimethylamino)methyl]-furfuryl alcohol.

EXAMPLE 4

Synthesis of Aminomethylfurans from Fructose in an Inert Solvent

Crystalline fructose (10 g) was placed in a 100 mL reaction vessel with PEGE-500 (50 g), (a polyethylene glycol dimethyl ether polymer having an average molecular weight of about 500), dimethylformamide (13 g), sulfuric acid (0.20 mL), and G-69B catalyst (0.50 g). The solution was heated to 180° C. for 3 hours. The solution was allowed to cool to room temperature and filtered to remove the resin catalyst. GC/MS indicated complete conversion of fructose and formation of 5-[(dimethylamino)methyl]-furfuryl alcohol.

EXAMPLE 5

Synthesis of Aminomethylfurans from Fructose using a Combination of Catalysts Crystalline fructose (10 g) was placed in a 100 mL reaction vessel with 3.7% $H_2SO_4$ (db), 5.0% G-69B catalyst (db) and pressurized to 1000 psi $H_2$ at 180° C. for 3 hrs. The solution was allowed to cool to room temperature and filtered to remove the catalyst. GC/MS indicated complete conversion of fructose and formation of 5-[(dimethylamino)methyl]-furfuryl alcohol and bis(dimethylaminomethyl)furan.

EXAMPLE 6

Preparation of Tetrahydrofuran Dimethanol Derivatives from Fructose

This example illustrates the effect of bifunctional resin on the dehydration of fructose to HMF followed by reduction to give furan dimethanol (FDM). Crystalline fructose (50.21 g) was placed in a 1 L reaction vessel with DMF (500 mL) and CH10 resin from Rohm and Haas (10.36 g) and pressurized to 500 psi hydrogen. The solution was heated to 100° C. for 3 hours. The reaction was allowed to cool to ambient temperature and filtered to remove the resin. GC/MS confirmed the formation of FDM.

EXAMPLE 7

Synthesis of Tetrahydrofuran Dimethanol Derivatives from Fructose

Crystalline fructose (30 g) was placed in a 1 L reaction vessel with ethanol (300 g) and CH28 resin (10 g). The solution was heated to 130° C. for 2 hours at 800 psi $H_2$. The solution was allowed to cool to room temperature, filtered to remove the resin catalyst, and ethanol was removed by rotary evaporation. GC/MS indicated formation of the 2,5-bis-(ethoxymethyl)tetrahydrofuran.

The foregoing examples are by way of illustration only and are not intended to limit the present invention in any way. In particular, although the amide solvent used in the examples was DMF, any amide of the formulas previously stated herein would form different alkyl amide derivatives with similar facility. Likewise, although the exemplary formation of the ether was with use of ethanol as the solvent, any other alcohol as previously mentioned herein could also be used and result in a different alkoxymethylfuran derivative. Moreover, even though the examples illustrate formation of the furan derivatives, the conditions are such that with extended time and/or higher pressure, the tetrahydrofuran derivatives would also be made. Accordingly, the invention may only be limited in accordance with the claims that follow.

What is claimed is:

1. A method of making an alkyl substituted amino furan compound of a formula selected from the group consisting of:

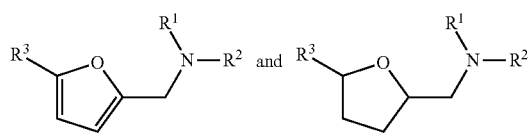

where $R^1$ is a $C_1$-$C_4$ alkyl group, $R^2$ is the same $C_1$-$C_4$ alkyl group or H, and $R^3$ is H or hydroxymethyl;
comprising, contacting a sugar, $H_2$, and an amide solvent of the formula:

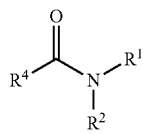

where $R^4$ is H, methyl or ethyl;
with a hydrogenation catalyst containing a metal comprising a member selected from the group consisting of Pd, Pt and Ni, and simultaneously with an acid catalyst, at a temperature, a pressure and for a time sufficient to form the amino furan derivative.

2. The method of claim 1 wherein the hydrogenation catalyst is a heterogeneous catalyst and the acid catalyst is a homogeneous mineral acid catalyst.

3. The method of claim 1 wherein the hydrogenation catalyst and the acid catalyst are heterogeneous catalysts.

4. The method of claim 3 wherein the hydrogenation catalyst and the acid catalyst are provided on a solid support.

5. The method of claim 1 wherein the hydrogenation catalyst is a heterogeneous catalyst and the metal comprises Pd.

6. The method of claim 1 wherein the hydrogenation catalyst is a heterogeneous catalyst comprising Pd and the acid catalyst is a heterogeneous catalyst comprising sulfonic acid.

7. The method of claim 6 wherein the hydrogenation catalyst and the acid catalyst are provided on a common solid support.

8. The method of claim 6 wherein the amide solvent is a dialkylformamide.

9. The method of claim 6 wherein the amide solvent is selected from the group consisting of dimethylformamide and dimethylacetamide.

10. The method of claim 6 wherein the amide solvent is dimethylformamide.

11. The method of claim 6 wherein the sugar is fructose, the amide solvent dimethylformamide and the furan amine is 5-[(mono-alkylamino)methyl]furfuryl alcohol.

12. The method of claim 11 wherein the amide solvent is selected from the group consisting of dimethylformamide and dimethylacetamide, and the alkylamino furan is selected from the group consisting of 5-[(methylamino)methyl]furfuryl alcohol and 5-[(dimethylamino)methyl]furfuryl alcohol.

13. The method of claim 10 wherein the hexose is fructose.

14. The method of claim 1 wherein the sugar is a pentose and the alkylamino furan is selected from the group consisting of 5-[(mono-alkylamino)methyl]furan and 5-[(di-alkylamino)methyl]furan.

15. The method of claim 14 the amide solvent is selected from the group consisting of dimethylformamide and dimethylacetamide, and the alkylamino furan is selected from the group consisting of 5-[(methylamino)methyl]furan and 5-[(dimethylamino)methyl]furan.

16. The method of claim 15 wherein the pentose is xylose.

17. The method of claim 1 wherein the sugar is fructose, the amide solvent is dimethylformamide, the hydrogenation catalyst is a heterogeneous catalyst containing Pd, the acid catalyst is a homogeneous mineral acid, and the alkylamino furan is 5-[(methylamino)methyl]furfuryl alcohol.

18. The method of claim 17 wherein the amide solvent is dimethylformamide.

19. The method of claim 1 wherein the sugar is fructose, the amide solvent is dimethylformamide, the hydrogenation catalyst is a heterogeneous catalyst on a resin containing Pd, the acid catalyst is a heterogeneous sulphonate catalyst on the same resin, and the alkylamino furan is 5-[(methylamino)methyl]furfuryl alcohol.

20. The method of claim 19 wherein the amide solvent is dimethylformamide.

21. The method of claim 1 wherein the amide solvent serves as a primary solvent in which the sugar is dissolved.

22. The method of claim 1 wherein the reaction solvent further includes a polyether based solvent.

23. The method of claim 1 wherein the sugar is dissolved in an inert polyethylene glycol based primary solvent.

* * * * *